United States Patent [19]

Müller et al.

[11] Patent Number: 6,127,307

[45] Date of Patent: Oct. 3, 2000

[54] CATALYST COMPOSITION FREE FROM NOBLE METALS

[75] Inventors: Ulrich Müller, Neustadt; Michael Schulz; Laszlo Marosi, both of Ludwigshafen; Wolfgang Harder, Weinheim, all of Germany

[73] Assignee: BASF Aktiengesellschaft, Ludwigshafen, Germany

[21] Appl. No.: 09/142,051

[22] PCT Filed: Mar. 5, 1997

[86] PCT No.: PCT/EP97/01113

§ 371 Date: Sep. 4, 1998

§ 102(e) Date: Sep. 4, 1998

[87] PCT Pub. No.: WO97/32866

PCT Pub. Date: Sep. 12, 1997

[30] Foreign Application Priority Data

Mar. 5, 1996 [DE] Germany ............................ 196 08 493

[51] Int. Cl.[7] .............................. B01J 31/00; B01J 27/24; B01J 27/14; B01J 27/192; B01J 23/00

[52] U.S. Cl. .......................... 502/162; 502/164; 502/167; 502/200; 502/208; 502/209; 502/210; 502/211; 502/212; 502/213; 502/302; 502/305; 502/325; 502/349; 502/353; 502/355

[58] Field of Search .................................. 502/162, 164, 502/167, 208–213, 305–355, 200, 302

[56] References Cited

U.S. PATENT DOCUMENTS

| | | | |
|---|---|---|---|
| 4,410,501 | 10/1983 | Taramasso et al. | 423/326 |
| 4,456,582 | 6/1984 | Marosi et al. | 423/277 |
| 4,871,701 | 10/1989 | Danner et al. | 502/62 |
| 4,897,498 | 1/1990 | Monnier et al. | 549/534 |
| 4,952,547 | 8/1990 | Annapragada et al. | 502/213 |
| 5,051,395 | 9/1991 | Mitchell et al. | 502/348 |
| 5,057,296 | 10/1991 | Beck | 423/277 |
| 5,057,481 | 10/1991 | Bhasin | 502/208 |
| 5,292,496 | 3/1994 | Nagashima et al. | 423/584 |
| 5,320,821 | 6/1994 | Nagashima | 423/584 |
| 5,401,486 | 3/1995 | Müller et al. | 423/705 |
| 5,859,265 | 1/1999 | Müller et al. | 549/531 |

FOREIGN PATENT DOCUMENTS

| | | |
|---|---|---|
| 1 265 810 | 2/1990 | Canada . |
| 100119 | 2/1984 | European Pat. Off. . |
| 109.273 | 5/1984 | European Pat. Off. . |
| 190 609 | 8/1986 | European Pat. Off. . |

(List continued on next page.)

OTHER PUBLICATIONS

Gustaaf Goor, et al., Ullmann's Encyclopedia of Industrial Chemistry, vol. A 13, pp. 443–466, "Hydrogen Peroxide", 1992 month not avail.

Gustaaf Goor, in G. Strukul (ed.), Catalytic Oxidations with Hydrogen Peroxide as Oxidant, pp. 13–43, "Hydrogen Peroxide: Manufacture and Industrial Use for Production of Organic Chemicals", 1992, month not avail.

K. Weissermel, et al., Industrielle Organische Chemie, pp. 284–289, "Umsetzungsprodukte Des Propens", 1988 month not avail.

(List continued on next page.)

Primary Examiner—Mark L. Bell
Assistant Examiner—Patricia L. Hailey
Attorney, Agent, or Firm—Oblon, Spivak, McClelland, Maier & Neustadt, P.C.

[57] ABSTRACT

A noble metal-free catalyst composition is obtainable by a) preparing an aqueous mixture comprising
  i) a salt of at least one base metal selected from among the elements having atomic numbers 21–32, 39–42, 48–51, 57–75 and 81–83;
  ii) phosphate ions; and
  iii) at least one nitrogen source; and
b) evaporating the aqueous mixture obtained and drying the catalyst composition thus formed. The catalyst composition prepared can be used for producing hydrogen peroxide and for the epoxidation of olefins.

13 Claims, 3 Drawing Sheets

FOREIGN PATENT DOCUMENTS

| | | |
|---|---|---|
| 537 836 | 4/1993 | European Pat. Off. . |
| 670 286 | 9/1995 | European Pat. Off. . |
| 4138155 | 11/1991 | Germany . |
| 4425672 | 7/1994 | Germany . |
| 4 407 326 | 3/1996 | Germany . |
| 05 017 106 | 1/1993 | Japan . |
| 2055821 | 3/1981 | United Kingdom . |

OTHER PUBLICATIONS

T. Tatsume, et al., J. Chem. Soc. Chem. Commun., pp. 1446–1447, "Hydroxylation of Benzene and Hexane by Oxygen and Hydrogen Over Palladium–Containing Titanium Silicalites", 1992 month not avail.

W. M. Meier, et al., Stickstoffbücherei, p. 148 (table of contents), "Atlas of Zeolite Structure Types", 1987 month not avail.

CATALYST COMPOSITION FREE FROM NOBLE METALS

BACKGROUND OF THE INVENTION

The present invention relates to a noble metal-free, solid catalyst composition, its preparation, its use for producing hydrogen peroxide and its use in the epoxidation of olefins.

1. Field of the Invention

Hydrogen peroxide is nowadays widely used as a clean oxidant, for example for the bleaching of paper and cellulose, for the removal of $SO_2$ from waste gases, in the electronics industry in semiconductor manufacture, and for sterilization, for example deodorization or disinfection of packing material. In organic chemistry, hydrogen peroxide is used particularly in epoxidation and hydroxylation reactions, where hydrogen peroxide can also be generated in situ.

2. Discussion of the Background

According to the prior art, hydrogen peroxide is nowadays prepared largely by the anthraquinone process (cf. Ullmann's Encyclopedia of Industrial Chemistry, 5th edition, vol. A13, pp. 443 ff). The substep of hydrogenation is here usually carried out in the presence of a metal catalyst such as palladium black or Raney nickel. In addition, heterogeneously catalyzed preparative processes in which noble metals on various supports are used as catalyst have been described. Thus, in U.S. Pat. No. 5,320,821, Pd/heteropolyacid is used as catalyst to prepare hydrogen peroxide from the elements. Furthermore, JP 5017106-A discloses the use of silica or zeolites together with platinum metals and EP 0 537 836 discloses the use of zirconium oxides together with Pd.

However, these processes often require the use of halogen compounds as promoters and stabilizers, as described, for example, in U.S. Pat. No. 5,320,821.

In organic oxidation reactions, it is possible to use hydrogen peroxide formed catalytically in situ directly or in combination with peroxo-oxygen transferers (cf. G. Goor in G. Strukul, "Catalytic Oxidations with Hydrogen Peroxide as Oxidant", pp. 13–43, 1992 Kluwer Academic Publishers). In particular, known heterogeneous oxidation catalysts are titanium-containing zeolites whose preparation is described, for example, in DE 3047798. Zeolites of this type are used to transfer oxygen to monoolefins and diolefins (cf. EP 0 100 119 and EP 0 190 609). Compared with the industrial oxidation by the chlorohydrin process (cf. K. Weissermel, H.-J. Arpe, "Industrielle Organische Chemie", 3rd edition, VCH Verlag (1998) pp. 284–289), the process according to EP 0 100 119 has the advantage of making, for example, propylene oxide obtainable in high selectivity from propene. In J. Chem. Soc. Chem. Commun. (1992) 1446–7), Tatsumi describes the hydroxylation of benzene and the oxidation of hexane using hydrogen/oxygen over metallic palladium on TS-1 silicalite, but only low reaction rates compared with hydrogen peroxide are observed.

In addition, DE-A 44 25 672 discloses improved noble metal catalysts containing titanium zeolites and processes for preparing propylene oxide from hydrogen, oxygen and propene. The catalyst systems described therein are very satisfactory, for example, in terms of reactivity, selectivity and stability. However, they nevertheless have the disadvantage, like other heterogeneous oxidation catalysts known from the prior art, of containing an expensive noble metal as catalytically active constituent. This is a significant economic disadvantage, particularly for the large-scale industrial production of the oxidation products such as propylene oxide.

SUMMARY OF THE INVENTION

It is an object of the present invention to provide a noble metal-free heterogeneous catalyst which is also essentially free of halogen atoms and can be employed both in the preparation of hydrogen peroxide and also in the catalytic oxidation of organic molecules such as, in particular, the epoxidation of olefins.

We have found that this object is achieved by a solid catalyst composition comprising a base metal component, phosphate and a nitrogen component as essential constituents.

Figure 1:
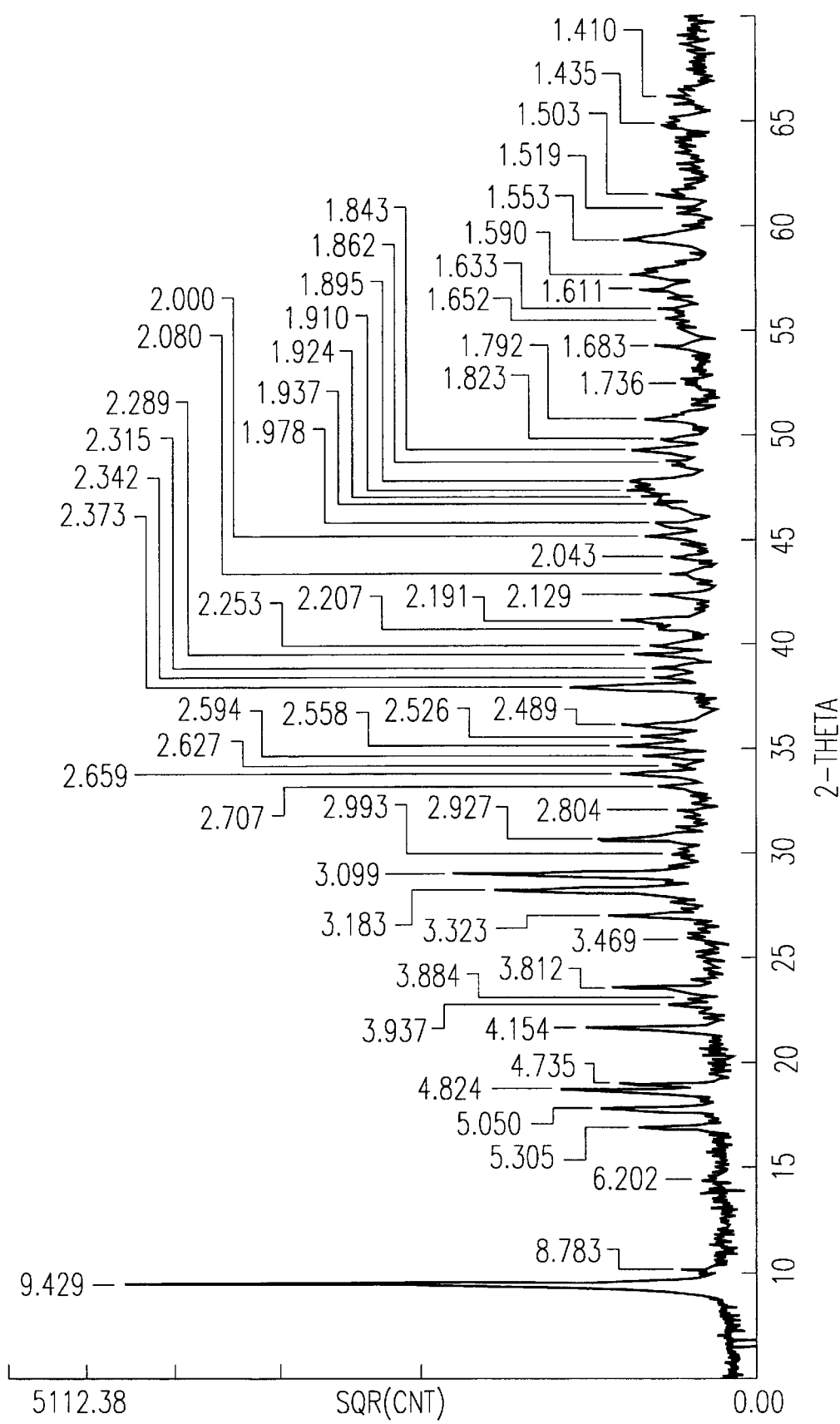
FIG. 1 shows an x-ray diffractogram of the product of Example 1.

Metals suitable according to the present invention are the d and f elements, i.e. elements of the 4th to 6th period from the groups IIIB, IVB, VB, VIB, VIIB, IB, IIB, IIIA, IVA and VA of the Periodic Table, i.e. Sc, Ti, V, Cr, Mn, Cu, Zn, Ga, Ge, Y, Zr, Nb, Mo, Cd, In, Sn, Sb, La, Ce, Pr, Nd, Sm, Eu, Gd, Tb, Dy, Ho, Er, Tm, Yb, Lu,Hf, Ta, W, Re, Tl, Pb, Bi and additionally Fe, Co and Ni.

DETAILED DESCRIPTION OF THE INVENTION

The present invention accordingly provides a catalyst composition (hereinafter referred to as metal phosphate) which is obtainable by a) preparing an aqueous mixture comprising
   i) a salt of at least one base metal selected from among the elements having atomic numbers 21–32, 39–42, 48–51, 57–75 and 81–83;
   ii) at least one phosphate ion and
   iii) at least one nitrogen source; and
b) evaporating the aqueous solution obtained and drying the catalyst composition thus formed, with or without gentle warming, so as to retain its catalytic activity.

The aqueous mixture of stage a) is preferably obtained by dissolving the components i), ii) and iii) in an aqueous solvent such as water or an aqueous alcoholic, for instance an aqueous ethanolic, solvent. However, the preferred solvent is water. The components can be dissolved together or separately from one another. However, preference is given to separately preparing two solutions, one of which contains the base metal salt and the other contains the phosphate component, and subsequently combining the two solutions. The nitrogen source required can be present in one or both of the solutions.

In the preparation of the metal phosphate catalysts of the present invention it is advantageous to first dissolve the metal component in the form of readily soluble salts in aqueous solution and then to add the phosphate in dissolved form with steady stirring.

The method of selecting the most suitable pH and temperature range for the preparation of a particular catalyst composition is known to those skilled in the art. In the preparation of the component solutions or the aqueous mixture it is usually sufficient to work at from 10 to 60° C., preferably from about 20 to 30° C. However, depending on the solution behavior of the components used, heating of one component solution or of the aqueous mixture above the value mentioned can be employed. During the preparation of the component solutions or the mixture, particular measures for adjusting the pH are usually not necessary. However, depending on the solution behavior of individual components, the addition of pH-adjusting substances such as customary acids or bases, or customary buffer substances, can be advantageous.

The aqueous mixture produced as described in stage a) preferably comprises the base metal ions (M) such as metal cations, phosphate (P) and nitrogen source (N) in a molar ratio in the range of about 1:0.8–1.4:0.6–4.0, for example 1:1:1 or 1:1:4.

The respective concentration of the individual components present in the aqueous mixture of the present invention can vary within a wide range and is essentially determined by the solubility of the compounds used. However, it is advantageous to prepare aqueous solutions which are as concentrated as possible in order to keep the time and energy requirements for the evaporation of the aqueous mixture as low as possible, provided that the formation of the catalytically active metal phosphate of the present invention is not impaired thereby. Thus, for example, the metal component and the phosphate component can be present, independently of one another, in a concentration in the range from about 0.1 to about 1.5 mol/l, for example from about 0.25 to about 0.85 mol/l. The nitrogen source(s) can be present, for example, in a concentration in the range from about 0.1 to about 5 mol/l, for example from about 0.25 to about 3.5 M. When ammonium ions are used as nitrogen source, the metal component, phosphate and ammonium are preferably present in the mixture in approximately equimolar amounts, with the concentration of each of the three components being able to be from about 0.25 to about 0.85 mol/l.

During evaporation and drying of the aqueous mixture, the conditions are preferably selected such that complete loss of the nitrogen component from the catalyst composition is essentially avoided. In particular, the conditions should be selected so that the proportion of nitrogen in the catalyst composition after completion of drying is reduced by not more than about 20–90 mol %, preferably about 50–80 mol %, based on the nitrogen used.

Figure 3:
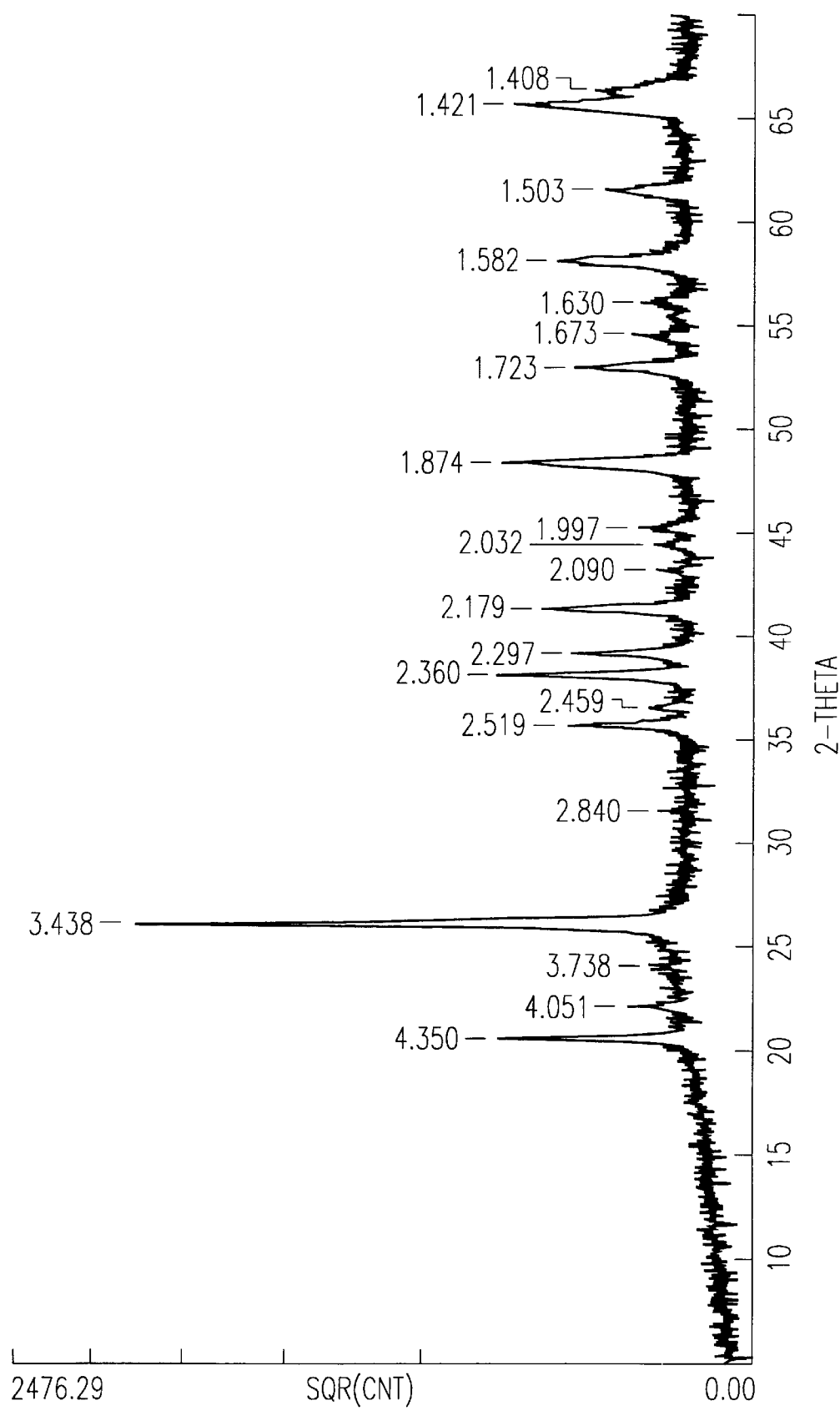
FIG. 3 shows an x-ray diffractogram of the product of Comparative Example 1.

The method of selecting the most suitable drying conditions for the particular catalyst material is known to those skilled in the art. As shown by the accompanying examples, it is possible, for example, for drying of the catalyst composition at a temperature which is too high to result in complete loss of nitrogen. This loss can be detected by means of a distinct, characteristic change in the X-ray diffraction patterns of the solid composition, as is shown by comparison of the attached X-ray diffractograms (FIG. 1 and FIG. 3). In particular, the fine structure in the diffractogram which is conspicuous for the catalytically active phosphates of the present invention can no longer be detected. However, the most significant effect of the loss of nitrogen is a decrease in or complete loss of the catalytic activity.

The catalytically active metal phosphate of the present invention is obtained, for example, when the aqueous mixture is first evaporated to dryness in a pressure range from about 10 to 1000 mbar, e.g. about 15–50 mbar, at from about 10 to about 200° C., e.g. about 100–140° C., and the residue obtained in this way is dried in air at atmospheric pressure at from about 30 about 200°C., preferably from about 50 to about 150° C., in particular from about 60 to about 140° C., e.g. 120° C. The drying time can be from about 5 to 20 hours, for example from about 8 to 12 hours.

This gives solid phases which are able to form hydrogen peroxide from hydrogen and oxygen by heterogeneous catalysis without noble metals and halogen-containing promoters.

In the catalyst composition thus prepared, base metal (M), phosphate (P) and nitrogen (N) can be present in a molar ratio of M:P:N=1:0.9–1.3:0.9–1.7, for example in a ratio of 1:1–1.3:1.1–1.5 or about 1:1.1–1.2:1.1–1.5.

For preparing the aqueous mixture as described in stage a), particular preference is given to using water-soluble base metal salts such as halides, e.g. fluorides, bromides or chlorides, hydroxides, nitrates, sulfates, cyanides or other water-soluble salts. The use of nitrates is particularly preferred. Base metals used are particularly elements having atomic numbers 21–32, 39–42 and 48–51. The oxidation state of the metal ion can vary and be, for example, +1, +2, +3, +4, +5, +6 or +7. However, preference is given to those oxidation states of which water-soluble salts exist.

According to a particularly preferred embodiment, use is made of salts of iron in the oxidation states +2, +3, +4, +5 or +6, in particular +2 or +3, and salts of tin in the oxidation states +2 or +4, in particular +2.

Most preferred is the use of water-soluble iron salts such as iron(III) nitrate and water-soluble tin salts such as tin(II) chloride.

Phosphate components which can be employed according to the present invention are metaphosphoric and orthophosphoric acid and the water-soluble, noble metal-free salts thereof. Particular preference is given to the use of water-soluble salts of orthophosphoric acid which form phosphate, hydrogenphosphate or dihydrogenphosphate ions in aqueous solution.

Nitrogen sources which can be employed according to the present invention are nitric acid and the water-soluble, noble. metal-free salts thereof. Preferred examples which may be mentioned are water-soluble nitrate salts of the abovementioned base metals. It is also possible to employ ammonia and the water-soluble, noble metal-free salts thereof. Also usable are primary, secondary or tertiary amines or salts thereof which are soluble in the solvent used according to the present invention. Examples which may be mentioned are lower alkylamines having up to 3 lower alkyl groups and lower alkylammonium salts having up to 4 lower alkyl groups. The lower alkyl groups are preferably $C_1$–$C_4$-alkyl groups such as methyl, ethyl, n-propyl and n-butyl.

The preparation of the nitrogen-containing metal phosphates of the present invention is preferably carried out using ammonium or lower alkylammonium phosphates. Particular preference is given to using ammonium dihydrogenphosphate.

According to a specific embodiment of the present invention, iron(III) nitrate and ammonium dihydrogenphosphate give, after drying, a catalyst composition which displays an X-ray diffractogram comprising the following characteristic diffraction lines:

| 2-Theta | d |
|---|---|
| 9.37 | 9.429 |
| 18.37 | 4.924 |
| 28.01 | 3.183 |
| 28.76 | 3.099 |
| 35.05 | 2.558 |
| 37.87 | 2.373 |

According to a further preferred embodiment of the invention, tin(II) chloride and ammonium dihydrogenphosphate give, after drying, a catalyst composition which displays an X-ray diffractogram comprising the following characteristic diffraction lines:

| 2-Theta | d |
|---------|-------|
| 12.79   | 6.915 |
| 13.04   | 6.784 |
| 19.09   | 4.645 |
| 20.21   | 4.389 |
| 23.01   | 3.861 |
| 23.90   | 3.720 |
| 26.18   | 3.400 |
| 30.33   | 2.944 |

Figure 2:
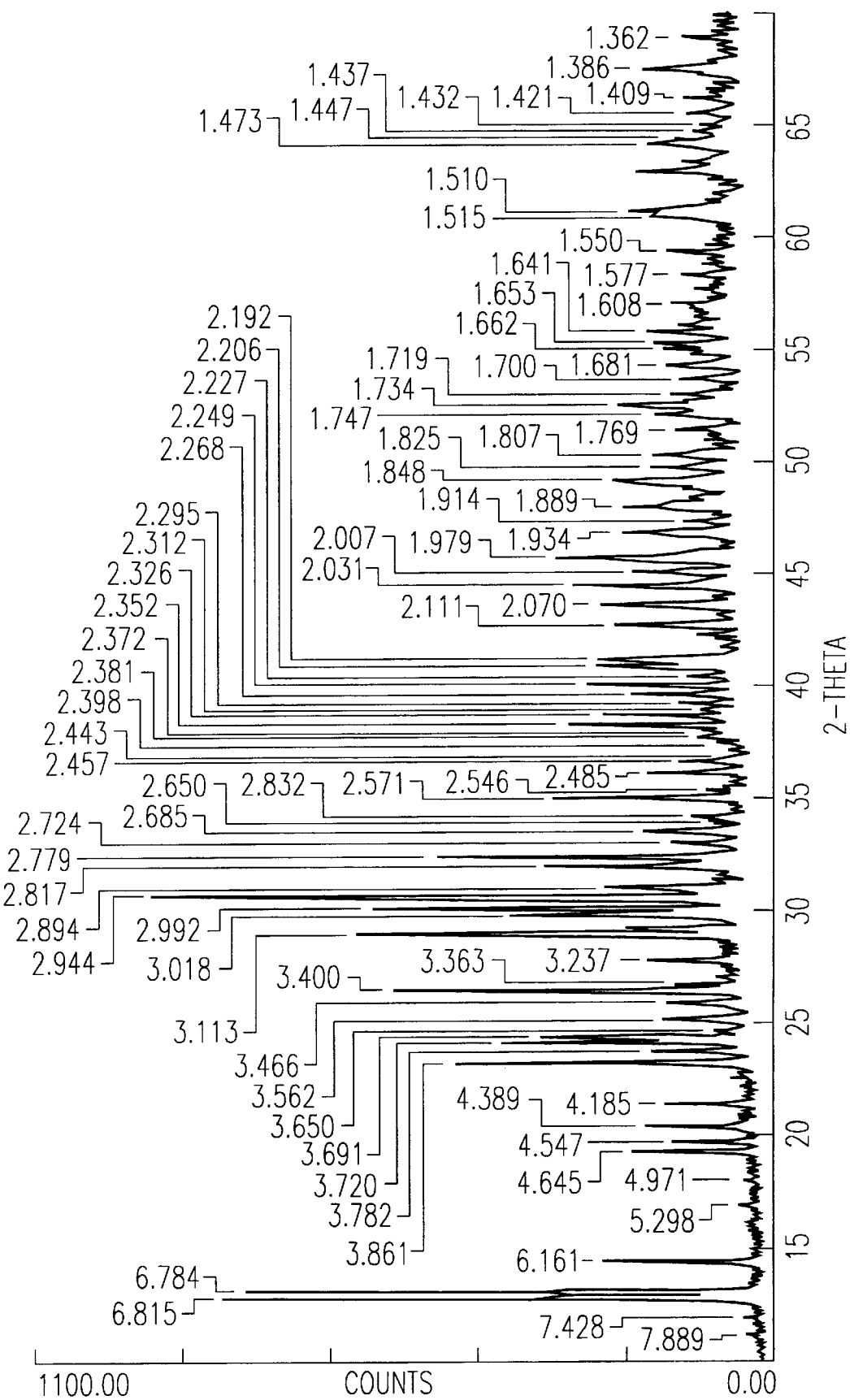
FIG. 2 shows an x-ray diffractogram of the product of Example 3.

The 2-theta values indicated above were determined using copper K(α) radiation (wavelength 1:1.54056 Ångström; wavelength 2:1.54439 Ångström). Further diffraction lines are shown in the accompanying FIGS. 1 and 2.

According to a further preferred embodiment, the catalytically active metal phosphate of the present invention is combined with an oxygen transferer as further catalytically active component. For this purpose, for example, the generally solid oxygen transferer can be suspended in the aqueous metal salt solution prepared as described in stage a) above and the suspension obtained in this way can, as described above, be evaporated and dried.

While the metal phosphate of the present invention is suitable, in particular, for use in processes for preparing hydrogen peroxide, the metal phosphate combined with the oxygen transferer is preferably used as heterogeneous catalyst in organic oxidation reactions, for example in the epoxidation of olefins.

The invention accordingly also provides a process for preparing hydrogen peroxide in which hydrogen and oxygen are reacted under conventional conditions in the presence of the metal phosphate of the present invention and the hydrogen peroxide formed is separated from the catalyst composition.

The invention additionally provides a process for the epoxidation of olefins which comprises reacting the olefin catalytically in the presence of hydrogen and oxygen. The olefin used can be any organic compound containing at least one ethylenically unsaturated double bond. It can be aliphatic, aromatic or cycloaliphatic in nature, and it can have a linear or branched structure. The olefin preferably contains from 2 to 30 carbon atoms. More than one ethylenically unsaturated double bond can be present, for example as in dienes or trienes. The olefin can additionally comprise functional groups such as halogen atoms, carboxyl groups, carboxylic ester functions, hydroxyl groups, ether bridges, sulfide bridges, carbonyl functions, cyano groups, nitro groups or amino groups.

Typical examples of such olefins are ethylene, propene, 1-butene, cis- and trans-2-butene, 1,3-butadiene, pentenes, isoprene, hexenes, octenes, nonenes, decenes, undecenes, dodecenes, cyclopentene, cyclohexene, dicyclopentadiene, methylenecyclopropane, vinylcyclohexane, vinylcyclohexene, allyl chloride, acrylic acid, methacrylic acid, crotonic acid, vinylacetic acid, allyl alcohol, alkyl acrylates, alkyl methacrylates, oleic acid, linoleic acid, linolenic acid, esters and glycerides of such unsaturated fatty acids, styrene, α-methylstyrene, divinylbenzene, indene and stilbene. Mixtures of said olefins can also be epoxidized by the process of the present invention.

The process of the present invention is particularly suitable for the epoxidation of propene to give propylene oxide.

For this purpose, the metal phosphate of the present invention combined with the oxygen transferer is advantageously used as catalyst. While the metal phosphate component catalyses the in situ production of hydrogen peroxide, the olefin is epoxidized with the aid of the transferer component.

It is here economically advantageous to allow the reaction to proceed only in a pressure range of about 1–20 bar at about 5–70° C., in particular at about 20–55° C. The molar ratio of $H_2:O_2$ can be varied in the range from about 1:1 to about 1:20, in particular from about 1:1 to about 1:10.

Oxygen transferers which can be used in the catalysts of the present invention are, for example, titanium silicates having a pentasil structure. As examples of silicates, particular mention may be made of those which are assigned X-ray crystallo-graphically to the MFI or MEL structures or MFI/MEL mixed structure. Zeolites of this type are described, for example, in W. M. Meier, D. H. Olson, "Atlas of Zeolite Structure Types", Butterworths, 2nd edition, 1987. It is also possible to use titanium-containing zeolites having the structure of ZSM-48, ferrierite, ZSM-12 or β-zeolite. In place of the titanium, it is also possible for, for example, vanadium to be present in bonded form in the zeolite. Likewise, titanium-, vanadium-, molybdenum-, rhenium- or tungsten-containing mesoporous oxides as described in U.S. Pat. No. 5057296 or DE-A 4407326 can also be used.

The abovementioned, particularly preferred titanium silicates having an MFI pentasil structure are prepared by crystallizing a synthesis gel comprising water, a titanium source and silicon dioxide in an appropriate manner with addition of organic, nitrogen-containing compounds under hydrothermal conditions, with or without the addition of ammonia solution, alkali or fluoride as mineralizer. Suitable nitrogen-containing compounds are, for example, 1,6-diaminohexane (cf. EP 0 007 081) or preferably the salts, or the free hyroxide of tetraalkylammonium salts, such as in particular tetrapropylammonium (TPA) (cf. DE-A 3047798). As described in DE-A 4138155, the use of expensive TPAOH can be avoided if TPABr together with ammonia are used in its place. The latter method in particular avoids alkali contamination of the titanium silicate; alkali contents of <100 ppm are desirable in order to later obtain a sufficiently active epoxidation catalyst.

The crystallization of the single-phase titanium silicate having the MFI structure is preferably carried out at 140–190° C., particularly advantageously at 175° C., over a period of from about 2 to 7 days, with well crystallized product being obtained after only about 4 days. Vigorous stirring and a high pH of about 12–14 during the crystallization can distinctly reduce both the synthesis time and the crystallite size.

It is advantageous to obtain, for example, primary crystallites having a particle size of from 0.05 to 0.5 $\mu$m, but in particular less than 0.2 $\mu$m.

After the crystallization, the titanium silicate can be filtered off, washed and dried at 100–1200° C. by methods known per se. To remove the amine or tetraalkylammonium compound still present in the pores, the material can be subjected to a further thermal treatment in air or under nitrogen. It is here advantageous to limit the temperature rise to <550° C.

The presence of the catalyst functions necessary for the olefin oxidation can be checked by IR spectroscopy; at 550 $cm^{-1}$ and 960 $cm^{-1}$ there are significant bands which indicate the presence of the desired solid state crystallinity and also the necessary epoxidation activity.

Titanium zeolites prepared in this way can, according to a preferred embodiment, be added to the metal phosphates of the present invention. For this purpose, for example, the solution of a metal nitrate and ammonium phosphate can be initially charged and the freshly calcined titanium zeolite can then be added in portions while stirring. The zeolite suspension can then be evaporated at about 30–200° C., in particular from about 50 to 100° C., under atmospheric or reduced pressure.

To modify the catalyst compositions of the present invention, the methods known from the prior art can be employed. Examples which may be mentioned are shaping with the aid of a binder, ion exchange and/or impregnation with metals, surface modification, for example by means of CVD (Chemical Vapor Deposition) or chemical derivative formation, for instance silylation. It is also conceivable to deposit the catalyst composition of the present invention on a solid, inert support. Suitable inert supports are, for example, spheres, pellets or extrudates of aluminum oxide or silicon dioxide. To prepare the supported catalyst composition of the present invention, it is possible, for example, to add the support particles to the abovementioned aqueous metal salt solution prior to evaporation, if desired together with the abovedescribed oxygen transferer, and to evaporate and dry the mixture as described above.

Depending on the organic molecule to be reacted, the catalysts of the present invention can be used in the liquid or gas phase or else. in the supercritical phase. In the case of liquid phases the catalyst is preferably used as a suspension, while in the gas-phase or supercritical procedure a fixed bed arrangement is advantageous.

Deactivated catalysts can be reconverted into an active form by controlled burning off of carbon deposits and subsequent reduction, for example using hydrogen. In the case of a low level of deposits, the catalyst can also be regenerated by a simple washing process. The washing process can be carried out as required at neutral, acid or basic pH. It may also be possible to restore the catalyst activity by means of a hydrogen peroxide solution acidified with mineral acid.

The present invention is illustrated by the following examples.

EXAMPLE 1

Preparation of an Iron Phosphate Catalyst (catalyst A)

In a polypropylene beaker, 116 g (0.33 mol) of iron(III) nitrate hexahydrate (Riedel de Haen) are dissolved at room temperature in 250 ml of deionized water and transferred to a 1 l glass flask provided with stirring. Separately therefrom, 38.3 g (0.33 mol) of ammonium dihydrogenphosphate ($NH_4H_2PO_4$) (Merck) are dissolved at room temperature in 150 ml of deionized water and the phosphate solution formed is added dropwise while stirring vigorously to the iron nitrate solution.

The solution thus formed is stirred for one further hour at room temperature. The reddish solution is then transferred to a rotary evaporator and evaporated at 90° C. and 15–20 mbar. The solid obtained is dried overnight at 120° C. in air in a convection drying oven. The product displays the X-ray diffractogram shown in FIG. 1. The 2-theta values obtained and the associated d values and the relative intensities for the diffraction lines determined are summarized in Table I below.

TABLE I

| Peak number | 2-Theta[a] | d | % | Peak Number | 2-Theta[a] | d | % |
|---|---|---|---|---|---|---|---|
| 1 | 9.372 | 9.4287 | 100.00 | 28 | 38.864 | 2.3153 | 2.46 |
| 2 | 10.063 | 8.7830 | 1.08 | 29 | 39.445 | 2.2825 | 2.27 |
| 3 | 14.270 | 6.2015 | 0.58 | 30 | 39.540 | 2.2773 | 2.24 |
| 4 | 16.698 | 5.3049 | 3.13 | 31 | 39.979 | 2.2533 | 2.54 |
| 5 | 17.546 | 5.0504 | 5.45 | 32 | 40.858 | 2.2068 | 1.99 |
| 6 | 18.378 | 4.8236 | 8.66 | 33 | 41.172 | 2.1907 | 4.01 |
| 7 | 18.723 | 4.7354 | 4.23 | 34 | 42.423 | 2.1290 | 2.43 |
| 8 | 21.371 | 4.1543 | 5.98 | 35 | 43.475 | 2.0799 | 1.19 |
| 9 | 22.564 | 3.9373 | 1.60 | 36 | 44.307 | 2.0427 | 1.36 |
| 10 | 22.878 | 3.8839 | 1.16 | 37 | 45.296 | 2.0004 | 2.85 |
| 11 | 23.318 | 3.8117 | 4.15 | 38 | 45.845 | 1.9777 | 1.91 |
| 12 | 25.657 | 3.4692 | 0.64 | 39 | 46.866 | 1.9370 | 2.05 |
| 13 | 26.803 | 3.3235 | 4.81 | 40 | 47.211 | 1.9236 | 2.99 |
| 14 | 28.012 | 3.1827 | 17.15 | 41 | 47.572 | 1.9098 | 3.49 |
| 15 | 28.781 | 3.0994 | 23.32 | 42 | 47.980 | 1.8945 | 3.60 |
| 16 | 29.827 | 2.9930 | 1.52 | 43 | 48.885 | 1.8616 | 1.38 |
| 17 | 30.518 | 2.9268 | 5.15 | 44 | 49.403 | 1.8432 | 3.37 |
| 18 | 31.884 | 2.8045 | 1.36 | 45 | 49.984 | 1.8232 | 1.72 |
| 19 | 33.061 | 2.7072 | 1.72 | 46 | 50.926 | 1.7916 | 2.77 |
| 20 | 33.673 | 2.6594 | 4.07 | 47 | 52.684 | 1.7359 | 0.97 |
| 21 | 34.097 | 2.6273 | 1.55 | 48 | 54.474 | 1.6830 | 1.44 |
| 22 | 34.553 | 2.5937 | 2.63 | 49 | 55.583 | 1.6520 | 1.08 |
| 23 | 35.055 | 2.5577 | 3.87 | 50 | 56.274 | 1.6334 | 2.13 |
| 24 | 35.505 | 2.5263 | 2.77 | 51 | 57.138 | 1.6107 | 2.13 |
| 25 | 36.054 | 2.4890 | 3.85 | 52 | 57.938 | 1.5904 | 3.02 |
| 26 | 37.875 | 2.3734 | 8.33 | 53 | 59.477 | 1.5529 | 3.54 |
| 27 | 38.409 | 2.3417 | 1.88 | 54 | 60.963 | 1.5185 | 1.41 |
|  |  |  |  | 55 | 61.654 | 1.5031 | 1.38 |
|  |  |  |  | 56 | 64.950 | 1.4346 | 1.58 |
|  |  |  |  | 57 | 66.206 | 1.4104 | 1.88 |

[a]The 2-theta values indicated above were determined using copper K(α) radiation (wavelength 1:1.54056 Ångström; wavelength 2:1.54439 Ångström).

The catalyst contains 22.2% by weight of iron, 14.0% by weight of phosphorus and 8.3% by weight of nitrogen, which corresponds to a molar ratio of Fe:P:N of about 1:1.13:1.5.

EXAMPLE 2

Use of the catalyst A according to the present invention for the catalytic production of hydrogen peroxide from the elements.

A steel autoclave fitted with a glass insert (25 ml capacity) is charged with the catalyst from Example 1 (100 mg) in 10 ml of methanol and the autoclave is closed. In an explosion-protected facility, hydrogen is fed in at 27° C. while stirring (30 min; 10 ml/min). The pressure is then increased to 40 bar using nitrogen and, finally, oxygen (100 ml/min) is metered in. After a reaction time of 4 hours, the autoclave is slowly vented and the contents are analyzed. 0.70% by weight of hydrogen peroxide are found by means of iodometric titration. The water content of the reaction product is 3.2% by weight.

EXAMPLE 3

Preparation of a Tin Phosphate Catalyst (catalyst B)

In a polypropylene beaker, 54.5 g (0.29 mol) of tin(II) chloride (Merck) are dissolved at room temperature in 250 ml of deionized water and transferred to a 2 l glass flask provided with stirring. In addition, 38.3 g (0.33 mol) of ammonium dihydrogenphosphate (Merck) are dissolved at room temperature in 950 ml deionized water and the phosphate solution is added dropwise while stirring vigorously to the tin chloride solution. The suspension formed is stirred at room temperature for a further period of one hour. The mixture is then transferred to a rotary evaporator and evaporated at 90° C. and 20 mbar and subsequently washed free of chloride using H$_2$O. The solid obtained is dried overnight at 120° C. in air in a convection drying oven. The product displays the X-ray diffractogram shown in FIG. 2. The 2-theta values determined and the associated d values and the relative intensities for the diffraction lines determined are summarized in Table II below.

TABLE II

| Peak number | 2-Theta[a] | d | % | Peak Number | 2-Theta[a] | d | % |
| --- | --- | --- | --- | --- | --- | --- | --- |
| 1 | 11.207 | 7.8890 | 3.77 | 24 | 28.986 | 3.0779 | 20.67 |
| 2 | 11.905 | 7.4280 | 4.84 | 25 | 29.578 | 3.0177 | 42.09 |
| 3 | 12.792 | 6.9147 | 85.68 | 26 | 29.838 | 2.9919 | 63.83 |
| 4 | 13.040 | 6.7835 | 84.93 | 27 | 30.335 | 2.9441 | 100.00 |
| 5 | 14.365 | 6.1607 | 26.59 | 28 | 30.867 | 2.8945 | 26.37 |
| 6 | 16.719 | 5.2982 | 5.27 | 29 | 31.742 | 2.8166 | 36.38 |
| 7 | 17.827 | 4.9713 | 4.41 | 30 | 32.180 | 2.7793 | 53.61 |
| 8 | 19.093 | 4.6445 | 23.14 | 31 | 32.850 | 2.7241 | 16.04 |
| 9 | 19.507 | 4.5469 | 14.75 | 32 | 33.347 | 2.6847 | 17.55 |
| 10 | 20.217 | 4.3888 | 20.34 | 33 | 33.797 | 2.6500 | 7.75 |
| 11 | 21.210 | 4.1854 | 13.89 | 34 | 34.033 | 2.6321 | 10.66 |
| 12 | 23.016 | 3.8669 | 50.81 | 35 | 34.861 | 2.5714 | 34.55 |
| 13 | 23.501 | 3.7823 | 19.16 | 36 | 35.228 | 2.5455 | 10.33 |
| 14 | 23.903 | 3.7196 | 44.03 | 37 | 36.115 | 2.4850 | 19.16 |
| 15 | 24.093 | 3.6908 | 38.00 | 38 | 36.541 | 2.4570 | 13.02 |
| 16 | 24.365 | 3.6502 | 8.72 | 39 | 36.754 | 2.4432 | 8.72 |
| 17 | 24.980 | 3.5617 | 16.68 | 40 | 37.464 | 2.3986 | 7.75 |
| 18 | 25.678 | 3.4664 | 16.58 | 41 | 37.744 | 2.3814 | 13.35 |
| 19 | 26.187 | 3.4002 | 57.59 | 42 | 37.898 | 2.3721 | 10.44 |
| 2D | 26.482 | 3.3629 | 15.93 | 43 | 38.241 | 2.3516 | 32.72 |
| 21 | 27.531 | 3.2372 | 18.95 | 44 | 38.678 | 2.3260 | 26.70 |
| 22 | 28.655 | 3.1127 | 66.52 | 45 | 38.927 | 2.3117 | 10.55 |
| 23 | 28.915 | 3.0853 | 22.82 | 46 | 39.223 | 2.2950 | 15.61 |

[a]The 2-theta values indicated above were determined using copper K(a) radiatiom (wavelength 1:1.54056 Ångström; wavelength 2:1.54439 Ångström).

The catalyst contains 37.0% by weight of tin, 11.2% by weight of phosphorus and 5.1% by weight of nitrogen, which corresponds to a molar ratio of Sn:P:N of about 1:1.16:1.16.

EXAMPLE 4

Use of the catalyst B according to the present invention for the catalytic production of hydrogen peroxide from the elements.

A steel autoclave fitted with a glass insert (25 ml capacity) is charged with the catalyst from Example 3 (100 mg) in 10 ml of methanol and the autoclave is closed. In an explosion-protected facility, hydrogen is fed in at 27° C. while stirring (30 min; 10 ml/min). The pressure is then increased to 40 bar using nitrogen and, finally, oxygen (100 ml/min) is metered in. After a reaction time of 4 hours, the autoclave is slowly vented and the contents are analyzed. 0.38% by weight of hydrogen peroxide are found by means of iodometric titration. The water content of the reaction product is 1.1% by weight.

EXAMPLE 5

Preparation of a titanium zeolite usable according to the present invention.

A four-neck flask (2 l capacity) is charged with 455 g of tetraethyl orthosilicate (Merck) at room temperature and 15 g of tetraisopropyl orthotitanate are added while stirring (250 rpm; blade stirrer) from a dropping funnel over a period of 30 minutes. A colorless, clear mixture is formed. Subsequently, 800 g of a tetrapropylammonium hydroxide solution (40% TPAOH, Alfa, diluted to 20% by weight with deionized water, alkali metal content <10 ppm) are subsequently added and the mixture is stirred for one further hour. Subsequently, the alcohol mixture (about 460 g) formed by hydrolysis is distilled off at from 90° to 100° C. 1.5 l of deionized water are added and the now slightly opaque sol is placed in a 2.5 l capacity stirring autoclave. The closed autoclave (anchor stirrer, 200 rpm) is heated at 3° C./min to a reaction temperature of 175° C. After 92 hours, the reaction is ended by cooling. The cooled reaction mixture (white suspension) is centrifuged and the solid is washed a number of times with water until neutral. The solid obtained is dried for 24 hours at 110° C. (yield 149 g). Subsequently, the template still present in the zeolite is burnt off in air by heating at 500° C. for 5 hours (calcination loss: 14% by weight).

The pure white product has, according to wet chemical analysis, a titanium content of 1.5% by weight and a residual alkali metal content (potassium) of <0.01% by weight. The yield is 97% based on SiO$_2$ used.

The cristallite size is about 0.1–0.15 µm and the product shows typical bands at 960 cm$^{-1}$ and 550 cm$^{-1}$ in the IR spectrum.

EXAMPLE 6

Preparation of an Iron Phosphate Epoxidation Catalyst According to the Present Invention In a polypropylene beaker, 116 g (0.33 mol) of iron(III) nitrate (Riedel de Haen) are dissolved in 250 ml of deionized water as described in Example 1. Separately therefrom, 38.3 g (0.33 mol) of ammonium dihydrogenphosphate are dissolved in water and the phosphate solution is added while stirring to the initially charged iron nitrate solution.

The pink solution formed is transferred to a rotary evaporator. In addition, a suspension of 7 g of titanium silicalite from Example 5 in 50 ml of deionized water is added and the suspension is evaporated over a period of 5 hours as described in Example 1. The catalyst is subsequently dried overnight at 120° C.

The catalyst contains 10.1% by weight of iron, 6.8% by weight of phosphorus, ?% by weight of nitrogen and 1.1% by weight of titanium.

EXAMPLE 7

Preparation of Propylene Oxide

In an explosion-protected facility, a glass pressure autoclave is charged with 60 ml of a 50% strength aqueous methanol solution. 1 g of the catalyst from Example 6 is added thereto. After heating the catalyst-containing suspension in the closed autoclave to about 40–50° C., nitrogen (30 ml/min), oxygen (30 ml/min), hydrogen (60 ml/min), propene (20 ml/min) are metered in while maintaining a constant pressure of 1 bar. After 2 hours, the off-gas stream of the reactor contains, according to gas chromatography, a C3 fraction comprising 101 ppm of propylene oxide as well as 17.7% by volume of propene and 0.11% by volume of propane. These values are still observed after 6 hours.

After the end of the reaction, 260 ppm of propanediol are also detected in the liquid reaction product.

COMPARATIVE EXAMPLE 1

Influence of the drying temperature on the catalytic activity of the catalysts of the present invention.

Example 1 is repeated, except that the solid obtained is additionally calcined at 550° C. in air for 5 hours.

The calcination loss is 58% by weight based on the initial weight of marterial. Nitrogen is no longer detected. The product now displays the distinctly changed X-ray diffractogram shown in FIG. 3. The 2-theta values determined and the associated d values and the relative intensities of the diffraction lines determined are summarized in Table III below.

TABLE III

| Peak number | 2-Theta[a] | d | % |
|---|---|---|---|
| 1 | 20.400 | 4.3499 | 17.26 |
| 2 | 21.922 | 4.0511 | 2.25 |
| 3 | 23.783 | 3.7382 | 2.19 |
| 4 | 25.897 | 3.4375 | 100.00 |
| 5 | 31.470 | 2.8404 | 1.42 |
| 6 | 35.615 | 2.5188 | 9.04 |
| 7 | 36.517 | 2.4586 | 2.25 |
| 8 | 38.096 | 2.3602 | 17.43 |
| 9 | 39.195 | 2.2965 | 8.87 |
| 10 | 41.394 | 2.1794 | 10.82 |
| 11 | 43.246 | 2.0903 | 1.54 |
| 12 | 44.543 | 2.0324 | 2.54 |
| 13 | 45.388 | 1.9965 | 2.19 |
| 14 | 48.546 | 1.8738 | 14.24 |
| 15 | 53.113 | 1.7229 | 8.33 |
| 16 | 54.824 | 1.6731 | 1.89 |
| 17 | 56.403 | 1.6300 | 1.65 |
| 18 | 58.292 | 1.5816 | 9.52 |
| 19 | 61.647 | 1.5033 | 4.73 |
| 20 | 65.650 | 1.4210 | 14.89 |
| 21 | 66.327 | 1.4081 | 5.44 |

[a]The 2-theta values indicated above were determined using copper K($\alpha$) radiation (wavelength 1:1.54056 Ångström; wavelength 2:1.54439 Ångström).

COMPARATIVE EXAMPLE 2

Use of the nitrogen-free comparative catalyst for the catalytic production of hydrogen peroxide from the elements.

Example 2 is repeated, but the catalyst from Comparative Example 1 (100 mg) is now initially charged. After a reaction time of 4 hours, the autoclave is slowly vented and the contents are analyzed. Only 0.17% by weight of hydrogen peroxide are found by means of iodometric titration. The water content of the reaction product is 2.1% by weight.

COMPARATIVE EXAMPLE 3

Preparation of a phosphate catalyst without a metal component according to the present invention.

In a polypropylene beaker, 18.9 g (0.3 mol) of boric acid (Merck) are dissolved at room temperature in 250 ml of deionized water and transferred to a 2 l glass flask provided with stirring. Separately therefrom, 38.3 g (0.33 mol) of ammonium dihydrogenphosphate (Merck) are dissolved at room temperature in 950 ml of deionized water and the phosphate solution is added dropwise while stirring vigorously to the boric acid solution. The suspension formed is stirred for a further period of one hour at room temperature. The mixture is then transferred to a rotary evaporator and evaporated at 90° C./20 mbar. The solid obtained is dried overnight in air at 120° C. in a convection drying oven.

The catalyst contains 6.1% by weight of boron, 20.7% by weight of phosphorus and 9.6% by weight of nitrogen.

COMPARATIVE EXAMPLE 4

Use of the catalyst from Comparative Example 3 for the catalytic production of hydrogen peroxide from the elements.

Example 2 is repeated, but the catalyst from Comparative Example 3 (100 mg) is now initially charged. After a reaction time of 4 hours, the autoclave is slowly vented and the contents are analyzed. only <0.01% by weight of hydrogen peroxide are found by means of iodometric titration. The water content of the reaction product is 0.6% by weight.

We claim:

1. A noble metal-free catalyst composition obtained by a process comprising:
    a) preparing an aqueous mixture comprising
        i) a salt of at least one base metal (M) selected from the group consisting of the elements having atomic numbers 21–32, 39–42, 48–51, 57–75 and 81–83;
        ii) phosphate ions (P); and
        iii) at least one nitrogen source (N); and
    b) evaporating the aqueous mixture obtained and drying the catalyst composition thus formed at a temperature of about 30 to about 200° C.
wherein base metal (M), phosphate (P) and nitrogen (N) are present in the noble metal-free catalyst composition in a molar ratio of M:P:N=1:0.9–1.3:0.9–1.7.

2. A catalyst composition as claimed in claim 1 wherein the aqueous solution comprises metal ions (M), phosphate ions (P) and a nitrogen source (N) in a molar ratio of M:P:N=1:0.8–1.4:0.6–4.0.

3. A catalyst composition as claimed in claim 1, wherein the base metal salt is selected from the group consisting of water-soluble salts of metals having atomic numbers 21–32, 39–42 and 48–51.

4. A catalyst composition as claimed in claim 1, wherein the nitrogen source is selected from the group consisting of nitric acid and the noble metal-free, water-soluble salts thereof, amines, ammonium or lower alkylammonium salts.

5. A catalyst composition as claimed in claim 4 wherein the nitrogen source is selected from the group consisting of water-soluble ammonium and lower alkylammonium salts or a water-soluble nitrate salt of the base metal used, and the phosphate component comprises dihydrogenphosphate ions.

6. A catalyst composition as claimed in claim 1, wherein the base metal salt is selected from the group consisting of salts containing iron in the oxidation state +2, +3, +4, +5 and/or +6 and salts containing tin in the oxidation state +2 and/or +4.

7. A catalyst composition as claimed in claim 1 wherein the aqueous mixture obtained from a) is evaporated at a pressure of from about 15 to about 1000 mbar and at from about 10 to about 200° C. and the residue thus obtained is dried at from about 30 to 200° C.

8. A catalyst composition as claimed in claim 1 wherein the base metal component present comprises iron ions and the composition displays an X-ray diffractogram comprising the following diffraction lines:

| 2-theta | d |
|---|---|
| 9.37 | 9.429 |
| 18.37 | 4.824 |
| 28.01 | 3.183 |
| 28.78 | 3.099 |
| 35.05 | 2.558 |
| 37.87 | 2.373 | or wherein the base metal component present comprises tin ions and the composition displays an X-ray diffractogram comprising the following diffraction lines:

| 2-theta | d |
|---------|-------|
| 12.79 | 6.915 |
| 13.04 | 6.784 |
| 19.09 | 4.645 |
| 20.21 | 4.389 |
| 23.01 | 3.861 |
| 23.90 | 3.720 |
| 26.18 | 3.400 |
| 30.33 | 2.944 |

9. A catalyst composition containing a noble metal-free catalyst component as claimed in claim 1, further comprising an oxygen transferer as a catalytically active component.

10. A catalyst composition as claimed in claim 9 wherein the oxygen transferer is selected from among organometallic compounds, zeolites, zeolite analogs, aluminophosphates or meso-porous metal oxides which each comprise at least one metal selected from among Ti, V, Mo, W, Re and Ru.

11. A catalyst composition as claimed in claim 10 wherein the oxygen transferer is a titanium or vanadium silicate having a pentasil structure.

12. A catalyst composition as claimed in claim 1 on a solid, inert support.

13. A catalyst composition comprising:
  i) a salt of at least one base metal (M) selected from the group consisting of the elements having atomic numbers 21–32, 39–42, 48–51, 57–75, and 81–83;
  ii) phosphate ions (P); and
  iii) at least one nitrogen source (N);
wherein said base metal (M), phosphate (P) and nitrogen (N) are present in the noble metal-free catalyst composition in a molar ratio of M:P:N=1:0.9–1.3:0.9–1.7.

* * * * *

UNITED STATES PATENT AND TRADEMARK OFFICE
CERTIFICATE OF CORRECTION

PATENT NO. : 6,127,307
DATED : October 3, 2000
INVENTOR(S) : Ulrich Mueller et al.

Page 1 of 1

It is certified that error appears in the above-identified patent and that said Letters Patent is hereby corrected as shown below:

Column 4,
Line 60, in table, "4.924" should read -- 4.824 --.
Line 62, in table, "28.76" should read -- 28.78 --.

Column 6,
Line 35, "the free hyroxide" should read -- the free hydroxide --.
Line 55, "100-200°C" should read -- 100-120°C --.

Column 9,
Line 23, "3.8669" should read -- 3.8609 --.
Line 32, "22.82" should read -- 22.32 --.

Column 10,
Line 40, delete "?% by weight".
Line 67, "marterial" should read -- material --.

Signed and Sealed this

Eighteenth Day of December, 2001

Attest:

JAMES E. ROGAN
*Attesting Officer*    *Director of the United States Patent and Trademark Office*